United States Patent [19]

Golik et al.

[11] Patent Number: 5,086,045
[45] Date of Patent: Feb. 4, 1992

[54] ANTITUMOR ANTIBIOTIC

[75] Inventors: Jerzy Golik, Southington, Conn.; John Beutler, Braddock Heights, Md.; Pat Clark, Frederick, Md.; John Ross, Myersville, Md.; John Roach; Gary Muschik, both of Frederick, Md.; William B. Lebherz, III, Woodsboro, Md.

[73] Assignee: Bristol-Myers Squibb Company, New York, N.Y.

[21] Appl. No.: 572,062

[22] Filed: Aug. 24, 1990

Related U.S. Application Data

[62] Division of Ser. No. 323,648, Mar. 15, 1989, Pat. No. 5,028,536.

[51] Int. Cl.$^5$ .................. A61K 31/715; A61K 31/70; C07G 11/00; C07G 3/00
[52] U.S. Cl. ........................ 514/61; 514/25; 536/6.5; 536/16.8; 536/17.2; 536/17.5; 536/17.6; 536/17.9; 536/18.1
[58] Field of Search ............ 536/6.5, 16.8, 17.2, 536/17.5, 17.6, 17.9, 18.1; 514/25, 61; 435/169, 101, 825, 128

[56] References Cited

U.S. PATENT DOCUMENTS

| 4,530,835 | 7/1985 | Bunge et al. | 424/117 |
| 4,661,353 | 4/1987 | Wilton et al. | 424/123 |
| 4,675,187 | 6/1987 | Konishi et al. | 424/117 |
| 4,837,206 | 6/1989 | Golik | 536/17.2 |

FOREIGN PATENT DOCUMENTS 2179649  8/1986  United Kingdom ............. 424/116

OTHER PUBLICATIONS

J. Antibiotics, 38 (11):1605–1609, (1985); J. Am. Chem. Soc., 109:3462–3464, (1987), J. Am. Chem. Soc., 109:3466–3468, (1987).
Program and Abstracts of 26th Interscience Conference on Antimicrobial Agents and Chemotherapy, Sep. 1986, Abstract 227.

*Primary Examiner*—Johnnie R. Brown
*Assistant Examiner*—Pamela S. Webber
*Attorney, Agent, or Firm*—David M. Morse; William T. Han

[57] ABSTRACT

An antitumor antibiotic designated BMY-41339 is produced by fermentation of certain strains of *Actinomadura verrucosospora*. BMY-41339 exhibits antimicrobial activity and also inhibits the growth of tumors in experimental animals.

3 Claims, No Drawings

ANTITUMOR ANTIBIOTIC

This application is a divisional of copending application Ser. No. 323,648, filed Mar. 15, 1989, now U.S. Pat. No. 5,028,536.

BACKGROUND OF THE INVENTION

1. Field of the Invention

The present invention relates to a novel antitumor antibiotic designated herein as BMY-41339 and to its preparation by fermentation of a BMY-41339-producing strain of *Actinomadura verrucosospora*.

2. Description of the Prior Art

BMY-41339 is a newly discovered bioactive compound of the BBM-1675 complex disclosed in U.S. Pat. No. 4,675,187. That patent discloses fermentation of *Actinomadura verrucosospora* strain H964-92 (ATCC 39334) or *Actinomadura verrucosospora* strain A1327Y (ATCC 39638) to produce a complex of potent antibiotic substances designated BBM-1675 complex and the separation of this complex into two major bioactive components, BBM-1675 $A_1$ and $A_2$, and four minor components, BBM-1675 $A_3$, $A_4$, $B_1$ and $B_2$.

U.S. Pat. No. 4,530,835 discloses (ermentation of Streptomvces sp. ATCC 39363 to produce the antitumor antibiotics designated CL-1577 A and B. The producing microorganism, ATCC 39363, is renamed *Actinomadura verrucaspora* subspecies *veractimycin* in U.S. Pat. No. 4,615,975. BBM-1675 $A_1$ and $A_2$ are believed to be identical respectively, to CL-1577 A and B.

*J. Antibiotics* 38 (11): 1605–1609 (1985) discloses isolation of another antitumor antibiotic, BBM-1675 $A_{1b}$, from the fermentation broth of *Actinomadura verrucosospora* strain H964-62 (ATCC 39334). It is believed that component $A_{1b}$ is identical to the antitumor antibiotic WS 6049-A disclosed in U.S. Pat. No. 4,578,271 as being produced by fermentation of Actinomadura pulveraceus ATCC 39100. WS 6049-A and B are related in structure to BBM-1675 $A_1$ and A2.

The structures of BBM-1675 $A_1$, $A_2$ and $A_{1b}$ have been elucidated and are disclosed in *J. Am. Chem. Soc.* 109:3462–3464 (1987). They are characterized by an unusual conjugated di-yne moiety which has also been found in the calichemicins (*J. Am. Chem. Soc.* 109:3466–3468, 1987) produced by a *micromonospora* strain (Program and Abstracts of 26th Interscience Conference on Antimicrobial Agents and Chemotherapy, Sept. 1986, Abstract 227).

A fragment of CL-1577 A or B designated CL-1577-B$_4$ is disclosed in U.S. Pat. No. 4,661,353 while fragments of BBM-1675 $A_1$ or $A_2$ designated BBM-1675 C and D are disclosed in U.K. Published Application 2,179,649 A.

Co-pending application Ser. No. 208,330 filed June 10, 1988 discloses the antitumor antibiotic designated BU-3420T having the formula

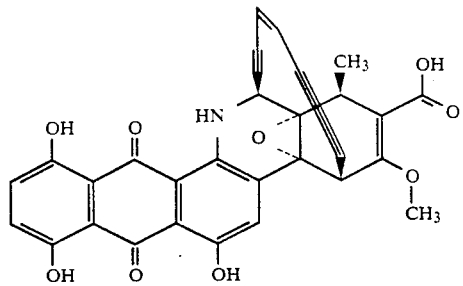

produced by fermentation of *Micromonospora chersina* ATCC 53710 and its triacetate derivative.

SUMMARY OF THE INVENTION

The present invention provides the antitumor antibiotic BMY-41339 and a process for its preparation and isolation in a purified state substantially free of co-produced substances. The antibiotic is obtained by cultivating a BMY-41339-producing strain of *Actinomadura verrucosospora* in an aqueous nutrient medium containing assimilable sources of carbon and nitrogen until a substantial amount of BMY-41339 is produced by said organism in said culture medium and then recovering the BMY-41339 from said culture medium substantially free of co-produced substances.

BMY-41339 has been found to exhibit antibacterial activity and to inhibit the growth of tumors in experimental animals.

DETAILED DESCRIPTION

The BMY-41339 antibiotic provided by the present invention has been determined to have the structure

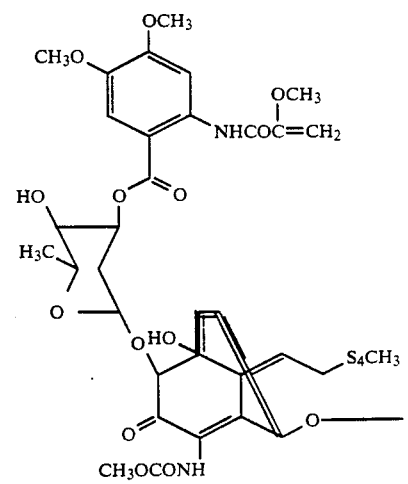

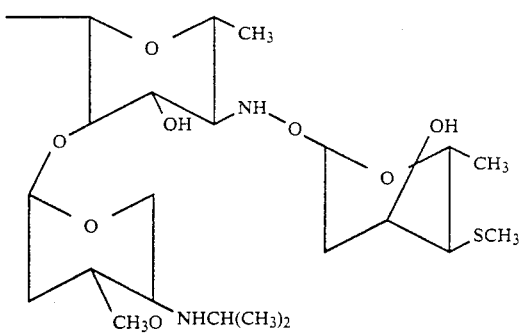

It has a molecular formula of $C_{59}H_{80}N_4O_{22}S_5$ and a molecular weight of 1357.65. Analysis for sulfur gave a value of 9.87% versus the calculated percentage of 11.3%.

The infrared absorption spectrum of BMY-41339 (KBr disc) shows characteristic infrared absorption bands at the following frequencies exhibited in reciprocal centimeters:

---
3534, 2955, 2920, 1720, 1670, 1590, 1575, 1405, 1425, 1395, 1350, 1290, 1230, 1190, 1135, 1095, 1050, 1000, 970, 730.
---

The ultraviolet absorption spectrum of BMY-41339 was determined in methanol. Observed absorption maxima and absorptivities were as follows:

| $\lambda_{max}$(nm) | Log E |
|---|---|
| 318 | 4.07 |
| 277 | 4.24 sh |
| 252 | 4.44 |

A proton magnetic resonance spectrum of BMY-41339 was determined on a solution of BMY-41339 in $CD_3OD$. Observed chemical shifts and pattern descriptions are as follows:

| Chemical Shift [ppm] | Multiplicity | Coupling Constants [Hz] |
|---|---|---|
| 8.46 | s | — |
| 7.65 | s | — |
| 6.64 | dd | 4.5, 10.5 |
| 6.22 | brd | 1.1 |
| 6.08 | d | 9.5 |
| 5.95 | dd | 1.5, 9.5 |
| 5.56 | brs | — |
| 5.53 | brd | 3.1 |
| 5.47 | dd | 2.8, 5.1 |
| 5.39 | d | 2.5 |
| 4.98 | dd | 1.7, 10.2 |
| 4.68 | d | 2.5 |
| 4.64 | q | 6.8 |
| 4.57 | d | 7.8 |
| 4.26 | s | — |
| 4.23 | m | — |
| 4.19 | d | 3.4 |
| 3.94 | s | — |
| 3.91 | s, 3H | — |
| 3.88 | m | — |
| 3.85 | s, 3H | — |
| 3.80 | s, 3H | — |
| 3.66 | brs | — |
| 3.5–3.65 | m | — |
| 2.98 | brm | — |
| 2.85 | brm | — |
| 2.62 | s, 3H | — |
| 2.42 | dd | 2.5, 4.1 |
| 2.36 | dd | 2.6, 10.5 |
| 2.32 | d | 3.7 |
| 2.25 | t | 9.8 |
| 2.13 | s, 3H | — |
| 1.95 | m | — |
| 1.59 | m, 2H | — |
| 1.38 | d, 3H | 6.2 |
| 1.32 | d, 3H | 6.1 |
| 1.26 | d, 3H | 6.5 |
| 1.13 | d, 3H | 6.2 |
| 1.07 | d, 3H | 6.3 |
| 0.8–1.0 | m (impurity) | — |

A carbon-13 nuclear magnetic resonance spectrum of BMY-41339 was determined on a solution of compound in $CDCl_3$. Observed chemical shifts were as follows:

13.7, 16.5, 17.5, 19.8, 22.2, 23.4, 23.5, 23.5, 29.0, 29.6, 34.0, 35.1, 40.1, 47.3, 52.6, 55.7, 56.0 (Double Int.), 56.1 (Double Int.), 62.4, 66.7, 68.2, 68.9, 69.2, 69.6, 70.2, 71.9, 76.1, 77.1, 83.5, 86.5, 88.5, 90.6, 97.2, 98.2, 99.6 (Double Int.), 103.8, 107.6, 112.6, 123.1, 124.9, 128.7, 129.8, 130.8, 136.7, 144.1, 154.0, 154.5, 160.7, 166.4, 174.9, 191.5.

When subjected to high pressure liquid chromatography (hplc) under the following conditions, BMY-41339 exhibits a retention time of 12.9 minutes with a peak area of 90% at 254 nm:

HPLC column: C-18 RP

Solvent system: Acetonitrile: methanol: 0.05M ammonium acetate (32.5:32.5.5:35 v/v)

Thermospray ionization mass spectrometry with the solvent system acetonitrile:methanol:water (33-33-34 v/v) at a flow rate of 1 ml/min (direct inlet) gave a molecular ion (M+H), m/z = 1357.

BMY-41339 has been discovered by the present inventors to be a minor component of the fermentation of *Actinomadura verrucosospora* ATCC 39334 disclosed in U.S. Pat. No. 4,675,187. That patent describes fermentation and isolation procedures for production of BBM-1675 $A_1$, $A_2$, $A_3$, $A_4$, $B_1$ and $B_2$, but does not disclose the novel BMY-41339 compound which is the subject of the present application.

Preparation of BMY-41339 according to the process of the present invention is described in detail below.

The Microorganism

The most preferred producing organisms are *Actinomadura verrucosospora* strain H964-92 which has been deposited in the American Type Culture Collection (Rockville, Maryland) under the accession number ATCC 39334 and *Actinomadura verrucosospora* strain A1327Y deposited under accession number ATCC 39638. A full description of these microorganisms is found in U.S. Pat. No. 4,675,187.

It is to be understood, however, that the present invention is not limited to use of the particular strains ATCC 39334 or 39638. It is especially intended to include other BMY-41339-producing variants or mutants of the deposited organisms which can be produced from the deposited organisms by known means such as x-radiation, ultraviolet radiation, treatment with nitrogen mustards, phage exposure and the like.

Production of the Antibiotic

BMY-41339 is produced by cultivating a BMY-41339-producing strain of *Actinomadura verrucosospora*, preferably *Actinomadura verrucosospora* ATCC 39334 or 39638 or a BMY-41339-producing mutant or variant thereof, in a conventional aqueous nutrient medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for production of large quantities of antibiotic, although for production of limited amounts surface cultures and bottles may also be used. The general procedure used for the cultivation of other actinomycetes are applicable to the present invention.

The nutrient medium should contain an appropriate assimilable carbon source such as glycerol, L(+)-arabinose, D-xylose, D-ribose, L-rhamnose, D-glucose, sucrose, cellobiose, soluble starch, D-mannitol or inositol. As nitrogen sources, ammonium chloride, ammonium sulfate, urea, ammonium nitrate, sodium nitrate, etc. may be used, either alone or in combination with organic nitrogen sources such as peptone, meat extract, yeast extract, corn steep liquor, soybean powder, cotton seed flour, etc. There may also be added, if necessary, nutrient inorganic salts to provide sources of sodium, potassium, calcium, ammonium, phosphate, sulfate, chloride, bromide, carbonate, zinc, magnesium, manganese, cobalt, iron and the like.

Production of the BMY-41339 antibiotic may be effected at any temperature conducive to satisfactory growth of the producing organism, e.g. 15°-45° C., and is conveniently carried out at a temperature of around 27°-32° C. Ordinarily, optimum production is obtained after incubation periods of about 8-10 days. When tank fermentation is to be carried out, it is desirable to produce a vegetative inoculum in a nutrient broth by inoculating the broth culture with a slant or soil culture or a lyophilized culture of the producing organism. After obtaining an active inoculum in this manner, it is transferred aseptically to the fermentation tank medium. Antibidtic production may be monitored by the paper disc-agar diffusion assay using *Staphylococcus aureus* 209P as the test organism.

Isolation and Purification 7 BMY-41339 is co-produced during fermentation as a minor component of the BBM-1675 complex. When fermentation is complete the BBM-1675 complex may be separated from the broth by conventional isolation procedures, e.g. solvent extraction with a suitable organic solvent such as ethyl acetate. The organic extract contains the whole BBM-1675 complex which may be precipitated from solution by addition of a suitable antisolvent such as n-hexane.

The various bioactive components in the BBM-1675 complex, including BMY-41339, may be separated and purified by conventional chromatographic procedures such as described in the examples which follow. BMY-41339 is co-purified with BBM-1675$A_1$, e.g. through chromatography on silica gel in successive chloroform-methanol-acetic acid solvent systems. In fact we have not detected BMY-41339 in admixture with BBM-1675 $A_1$ by normal phase silica chromatography - it is only revealed by analytical reverse-phase high pressure liquid chromatography (hplc) on octadecylsilyl silica media. Typically, the amount of BMY-41339 is 1-5% of the amount of BBM-1675 $A_1$ produced. These two compounds may be distinguished by their differing retention times in the reverse phase analytical hplc system. For example, using an eluant consisting of 32.5% acetonitrile, 32.5% methanol and 35% 50 mM aqueous ammonium acetate at pH 4.4, BBM-1675 $A_1$ elutes from a 10 cm × 0.46 cm column of NOVAPAK C18 (Waters Division, Millipore Corp.) with a retention time of 8.8 minutes, whereas BMY-41339 elutes with a retention time of 2.9 minutes. This difference in retention is exploited in the examples below during the preparative separation of BMY-41339 from BBM-1675 $A_1$.

Biological Properties of BMY-41339

Antimicrobial activity of BMY-41339 was determined for a variety of bacteria by the serial two-fold agar dilution method. As shown in the table below, BMY-41339 exhibits a broad spectrum of antibacterial activity.

| Antibacterial Activity of BMY-41339 | |
|---|---|
| Organism | MIC in mcg/ml BMY-41339 |
| E. faecalis A20688 | .002 |
| E. faecalis A25707 | .002 |
| E. faecalis A25708 | .002 |
| S. aureus A9537 | .001 |
| S. aureus A20698 | .001 |
| S. aureus A24407 | .001 |
| E. coli A15119 | .25 |
| E. coli A20697 | .25 |
| E. coli A9751 | .016 |
| K. pneumoniae A9664 | 1 |
| K. pneumoniae A20468 | 1 |
| P. vulgaris A21559 | .13 |
| P. aeruginosa A9843 | .25 |
| P. aeruginosa A20235 | .13 |
| P. aeruginosa A21508 | .25 |
| B. subtilis A9506-A | .001 |

The in vivo antitumor activity of BMY-41339 was determined in the standard P388 mouse leukemia model. A summary of the experiments performed using BMY-41339 is provided below.

Mice

DBA/2 and (Balb/c × DBA/2)$F_1$ (CDF$_1$) hybrid mice were purchased from Charles River Breeding Co. (Wilmington, MA). They were provided food and water ad libitum.

Tumor

The P388 murine ascites leukemia was maintained by weekly in vivo passage in DBA/2 mice.

Drug

Esperamicin $A_1$ and BMY-41339 were dissolved in ethanol. Further dilutions were made with 0.9% NaCl (saline) until the ethanol concentration (v/v) was 10%. All administrations were made, therefore, in a 10% ethanol in saline vehicle. For ip injections, the concentration of compound was adjusted according to the average initial body weight of each group of mice to be injected such that the desired dose would be contained in a 0.5 ml injection volume. The same procedure was used for iv compound administration except the injection volume was 0.2 ml.

Antitumor Assessment

Antitumor experiments were initiated by implanting $10_6$ P388 leukemia cells either ip or iv into $CDF_1$ mice. BMY-41339 and esperamicin $A_1$ (included as a positive reference compound), were injected either ip in mice implanted ip with P388, or iv in mice implanted iv with P388 on Day 2 post-implant only Eight different dose levels of BMY-41339, at two-fold increments, were evaluated in each of the two experiments performed.

Activity was judged on the basis of increased lifespan, which was determined by calculating the median survival time (MST) of drug-treated (T) mice divided by the MST of tumor control (C) mice, × 100, and expressed as % T/C. A % T/C value of ≧ 125 was considered indicative of activity in these models.

Results

In Experiment No. 8102, untreated leukemia control mice implanted ip with $10^6$ P388 cells had a Median Survival Time of 10 days. In comparison, mice treated on Day 2 only with single injections of BMY-41339 above 0.1 μg/kg had meaningful increases in lifespan as reflected by % T/C values of ≧ 135%. The highest dose tested, 3.2 μg/kg, caused a T/C of 140% (1.6 μg/kg caused a T/C of 145%), but no obvious sign of overt drug-associated toxicity (e.g. excessive body weight loss, early deaths) was observed, indicating the potential for further dose escalation. At these same doses BMY-41339 was not effective when given iv versus iv-implanted leukemia, but there was also no indication of having reached a maximum tolerated dose. BBM-1675A$_1$, included as a positive reference material, was active in both these models.

Experiment No. 8102

| Compound | Dose (mg/kg/dose) | | % T/C | Avg. wt. change on day 6 (grams) | Survivors on Day 5 Day 30 |
|---|---|---|---|---|---|
| (ip administration) | | | | | |
| BBM-1675 A$_1$ | 1.6 | M | 170 | −0.7 | 5/6 |
| | 0.8 | M | 160 | −0.6 | 6/6 |
| | 0.4 | M | 140 | −0.0 | 6/6 |
| | 0.2 | M | 140 | −0.6 | 6/6 |
| | 0.1 | M | 140 | 0.5 | 6/6 |
| | 0.05 | M | 130 | 0.5 | 6/6 |
| BMY-41339 | 3.2 | M | 140 | 0.7 | 6/6 |
| | 1.6 | M | 145 | −0.1 | 6/6 |
| | 0.8 | M | 140 | 0.4 | 6/6 |
| | 0.4 | M | 135 | 0.6 | 6/6 |
| | 0.2 | M | 140 | 0.6 | 6/6 |
| | 0.1 | M | 120 | 0.7 | 6/6 |
| | 0.05 | M | 110 | 1.3 | 6/6 |
| | 0.025 | M | 110 | 0.8 | 6/6 |
| Vehicle | | | 100 | 2.4 | 10/10 |
| (iv administration) | | | | | |
| BBM-1675A$_1$ | 1.6 | M | 125 | −0.2 | 6/6 |
| | 0.8 | M | 106 | 0.3 | 6/6 |
| | 0.4 | M | 106 | 0.3 | 6/6 |
| | 0.2 | M | 100 | −0.0 | 6/6 |
| | 0.1 | M | 100 | −0.2 | 6/6 |
| | 0.05 | M | 100 | 0.4 | 6/6 |
| BMY-41339 | 3.2 | M | 113 | −0.2 | 6/6 |
| | 1.6 | M | 100 | −0.1 | 6/6 |
| | 0.8 | M | 100 | −0.3 | 6/6 |
| | 0.4 | M | 100 | −0.4 | 6/6 |
| | 0.2 | M | 100 | −0.3 | 6/6 |
| | 0.1 | M | 106 | 0.4 | 6/6 |
| | 0.05 | M | 100 | 0.1 | 6/6 |
| | 0.025 | M | 100 | 0.4 | 6/6 |
| Vehicle | | | 100 | 1.1 | 10/10 |

In P388 Experiment No. 8109, untreated leukemia control mice implanted ip with $10^6$ P388 cells had an MST of 10.5 days. At higher doses than were evaluated in the previous study, BMY-41339 produced active increases in lifespan when 0.5 -32 μg/kg was administered. The best effect observed, a T/C of 171%, was obtained at the highest dose tested, 32 μg/kg. BBM-1675 A$_1$ was also active in this experiment in the i.v. P388 implanted portion of this experiment, BMY-41339 yielded active increases in lifespan at two dose levels evaluated; T/C values of 139 and 156% were associated with iv injections of 16 and 32 μg/kg, respectively, of BMY-41339. BBM-1675 A$^1$ was included in this study and was active at one of the doses tested. Untreated tumor control mice implanted iv with $10^6$ P388 cells had an MST of 9 days. Data for Experiment No. 8109 are shown below.

Experiment No. 8109

| Compound | Dose (mg/kg/dose) | | % T/C | Avg. wt. change on day 6 (grams) | Survivors on Day 5 Day 30 |
|---|---|---|---|---|---|
| (ip administration) | | | | | |
| BBM-1675 A$_1$ | 1.6 | M | 170 | −0.7 | 5/6 |
| | 0.8 | M | 160 | −0.6 | 6/6 |
| | 0.4 | M | 140 | −0.0 | 6/6 |
| | 0.2 | M | 140 | −0.6 | 6/6 |
| | 0.1 | M | 140 | 0.5 | 6/6 |
| | 0.05 | M | 130 | 0.5 | 6/6 |
| BMY-41339 | 3.2 | M | 140 | 0.7 | 6/6 |
| | 1.6 | M | 145 | −0.1 | 6/6 |
| | 0.8 | M | 140 | 0.4 | 6/6 |
| | 0.4 | M | 135 | 0.6 | 6/6 |
| | 0.2 | M | 140 | 0.6 | 6/6 |
| | 0.1 | M | 120 | 0.7 | 6/6 |
| | 0.05 | M | 110 | 1.3 | 6/6 |
| | 0.025 | M | 110 | 0.8 | 6/6 |
| Control | | | 100 | 2.4 | 10/10 |
| (iv administration) | | | | | |
| BBM-1675A$_1$ | 1.6 | M | 125 | −0.2 | 6/6 |
| | 0.8 | M | 106 | 0.3 | 6/6 |
| | 0.4 | M | 106 | 0.3 | 6/6 |
| | 0.2 | M | 100 | −0.0 | 6/6 |
| | 0.1 | M | 100 | −0.2 | 6/6 |
| | 0.05 | M | 100 | 0.4 | 6/6 |
| BMY-41339 | 3.2 | M | 113 | −0.2 | 6/6 |
| | 1.6 | M | 100 | −0.1 | 6/6 |
| | 0.8 | M | 100 | −0.3 | 6/6 |
| | 0.4 | M | 100 | −0.4 | 6/6 |
| | 0.2 | M | 100 | −0.3 | 6/6 |
| | 0.1 | M | 106 | 0.4 | 6/6 |
| | 0.05 | M | 100 | 0.1 | 6/6 |
| | 0.025 | M | 100 | 0.4 | 6/6 |
| Vehicle | | | 100 | 1.1 | 10/10 |

Conclusion

BMY-41339 is active against P388 leukemia based on confirmed experimental results. Most impressively, when adequate dosage was administered, BMY-41339 was active against the disseminated iv implanted P388 leukemia model.

As shown above BMY-41339 possesses antimicrobial activity against a broad spectrum of bacteria. The compound is thus useful in the therapeutic treatment of mammals and other animals for infectious diseases caused by such bacteria. Additionally, it may be used for other conventional applications of antimicrobial agents such as disinfecting medical and dental equipment.

The marked antitumor activity shown against experimental tumors in mice, e.g. P388 leukemia, indicates that BMY-41339 is therapeutically useful in inhibiting the growth of mammalian tumors.

The present invention, therefore, provides a method for therapeutically treating an animal host affected by a bacterial infection or by a malignant tumor which comprises administering to said host an effective antibacterial or tumor-inhibiting dose of BMY-41339 or a pharmaceutical composition thereof.

In another aspect the present invention provides a pharmaceutical composition which comprises an effective antibacterial or tumor-inhibiting amount of BMY-41339 in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the BMY-41339 antibiotic used will vary according to the particular composition formulated, the mode of application and the particular situs, host and disease being treated. Many factors that modify the action of the drug will be taken into account by those skilled in the art, for example, age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be ascertained by those skilled in the art using conventional dosage administration tests in view of the above guidelines.

The following examples are provided for illustrative purposes only and are not intended to limit the scope of the invention: All operations were carried out under yellow fluorescent lights (Sylvania Gold F40/60) due to the light-sensitivity of the bioactive components. Flash chromatography was carried out essentially as described by Still et al., with maximum loadings of 10 gm on a 10 cm diameter flash chromatography column. Mass recoveries were typically 90 percent of loading mass. Silica for flash chromatography was Merck No. 9385. Compressed nitrogen was used as a source of pressure. All fractions were evaporated to dryness at 35° C. and stored dry at −20°. Reverse-phase HPLC was carried out using a Waters Delta-Prep 4000, with a Rainin Dynamax C18 column (40 mm × 25 cm), with loadings of 250 mg per injection in 10 ml DMSO or acetonitrile. All purification solvents were HPLC grade (American Burdick & Jackson), while recovery solvents were technical or ACS grade. Purity of fractions was determined by analytical hplc on Waters Nova-Pak $C_{18}$ columns.

EXAMPLE 1

Fermentation of BMY-41339

Four plastic vials, stored at −70° C. and containing 5 ml each of a preparation of *Actinomadura verrucosospora* strain A1327Y (ATCC 39638), were thawed at 28° C. and used to inoculate 4X, 500 ml baffled Erlenmeyer flasks each containing 100 ml of seed medium (hereinafter referred to us as seed stage 1). The seed medium for this and subsequent flask seed stages consisted of an aqueous medium containing 10 g/L cotton seed meal, 20 g/L corn starch, 5 g/L glucose monohydrate, 10 g/L dried yeast and 2 g/L $CaCO_3$. The medium was pH adjusted to 7.0 prior to autoclaving. Seed stage 1 was incubated on a rotary shaker for two days at 28° C.

Three of the four flasks from seed stage 1 were used to inoculate each of three 4000 ml baffled Erlenmeyer flasks containing 2000 ml of media (hereinafter referred to as seed stage 2) prepared by materials and methods described in stage 1. Seed stage 2 was cultured for two days, at which time the contents of two of the four flasks were aseptically pooled (volume, 3-4 liters) into a sterile aspirator flask for use in inoculating the 1.0 liter seed fermentor.

The inoculum prepared in seed stage 2 was aseptically transferred into a 110 liter seed fermentor containing 68 liters of heat sterilized media (one hour at 121° C.) consisting of 10 g/L cotton seed meal, 20 g/L corn starch, 5 g/L glucose monohydrate, 10 g/L dried yeast, 2 g/L $CaCO_3$ and 2 ml/L polyglycol antifoam constituted in 68 liters of Reverse Osmosis Deionized (RODI) water. The medium was pH adjusted to 6.8–7.2 prior to sterilization. The inoculated culture was maintained at 28° C. and aerated at a rate of 73.6 liters/minute.

The seed fermentor was cultured for a period of 48 hours at which time the entire contents of the seed fermentor were aseptically transferred into a 1100 liter production fermentor containing 680 liters of sterile medium. The production medium consisted of 60 g/L cane molasses, 20 g/L corn starch, 20 g/L finely ground fish meal, 0.1 g/L $CuSO_4 \cdot 5H_2O$, 2 g/L $CaCO_3$, 0.5 mg/L NaI and 10 ml/L polyglycol antifoam constituted in 680 liters of RODI water (pH adjusted to 6.8–7.2 before sterilization). The production culture was aerated at a rate of 453 liters/minute and agitated at 180 RPMs. The culture was maintained at 28° C. for 8–10 days at which time the fermentation was terminated and the broth harvested for antibiotic recovery. The production of BMY-41339 may be affected by culture pH and/or the amount of oxygen available to the culture.

EXAMPLE 2

Isolation and Purification of BMY-41339

Whole broth (680 L) as obtained by the procedure of Example 1 was mixed with an equal volume of ethyl acetate. Diatomaceous earth was then added, the mixture was filtered through a diatomaceous earth bed on a filter press, and the phases were separated. The ethyl acetate phase was concentrated using a wiped-film evaporator and rotary evaporator to eight liters of an oil. Antifoam was largely removed by suspension of the oil in ten volumes of hexane and then filtration through a bag filter precoated with diatomite. The residual mass (236 g) was extracted with 19 liters of ethyl acetate and deposited on 2.4 kg of diatomite by evaporation with several cycles of slurrying in hexane and reevaporation. The diatomite was slurried in hexane into a chromatography column and eluted successively with 47 liters of hexane, 14 liters of hexane-toluene, 18 liters of methylene chloride, 18 liters of chloroform and 12 liters of methanol. BMY-41339 eluted in the methylene chloride fraction and on evaporation the solid mass of 33 grams contained >1% BMY-41339 at this point.

Flash Chromatrography

Chromatography over silica using chloroform-methanol (95:5 v/v) removed over 50% of the mass from the methylene chloride diatomite column eluate, including a major component, N-acetamido-p-hydroxybenzylamine. This left 12.8 gms of crude complex. A second step using hexane-acetone (1:1 v/v) removed most of the remaining contaminants, including a blue pigment, leaving 7.6 gms consisting mainly of BBM-1675 $A_1$ and $A_2$, with small amounts of BMY-41339. BBM-1675 $A_2$ was then efficiently removed by chromatography using chloroform-t-butanol (100:6 v/v), in which BBM-1675 $A_1$ and BMY-41339 migrated but BBM-1675 $A_2$ did not. A small quantity of brown pigment was removed in a final flash chromatography step using chloroform-methanol-acetic acid (95:5:0.1 v/v). This gave 5.5 gms of 97% pure BBM-1675 $A_1$ with approximately 3% BMY-41339.

Hplc and back extraction

Chromatography by reversed phase hplc over $C_{18}$ using methanol-acetonitrile-50 mM ammonium acetate pH 4.4 (32.5:32.5:35) gave a separation of $A_1$ from BMY-41339. Prompt dilution of the column effluent was done with equal volumes of chloroform and distilled water in a separatory funnel, extraction, phase separation and re-extraction with a second volume of chloroform. The combined chloroform phases were then evaporated to dryness. The BMY-41339 fraction at this point was approximately a 1:1 mixture of BMY-41339 and BBM-1675 $A_1$. Reverse phase rechromatography in the same solvent system provided pure BMY-41339 after an identical back extraction process.

We claim:

1. The antitumor antibiotic BMY-41339 having the formula

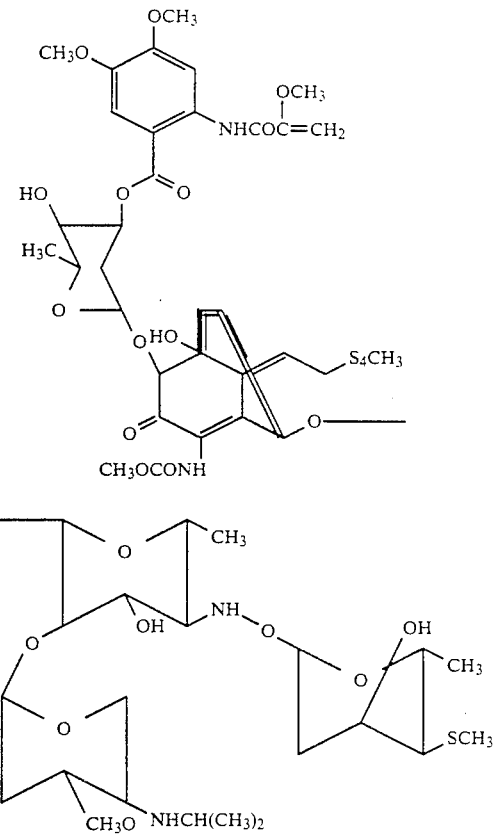

2. A pharmaceutical composition which comprises as an active ingredient BMY-41339 in combination with an inert pharmaceutically acceptable carrier or diluent.

3. A method for therapeutically treating an animal host affected by a bacterial infection, which comprises administering to said host an effective antibacterial dose of BMY-41339.

* * * * *

UNITED STATES PATENT AND TRADEMARK OFFICE
CERTIFICATE OF CORRECTION

PATENT NO. : 5,086,045

DATED : February 4, 1992

INVENTOR(S) : Jerzy Golik, et al

It is certified that error appears in the above-identified patent and that said Letters Patent is hereby corrected as shown below:

Column 2, line 50-65, that portion of the formula reading

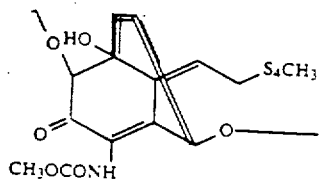

should read

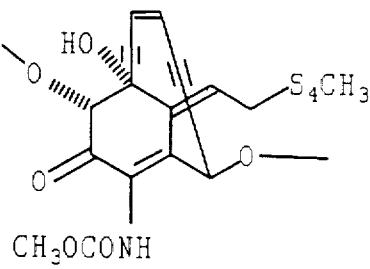

UNITED STATES PATENT AND TRADEMARK OFFICE
CERTIFICATE OF CORRECTION

PATENT NO.  : 5,086,045

DATED       : February 4, 1992

INVENTOR(S) : Jerzy Golik, et al

It is certified that error appears in the above-identified patent and that said Letters Patent is hereby corrected as shown below:

Column 12,

Claim 1, that portion of the formula reading

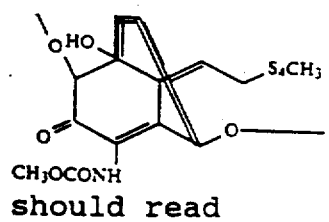

should read

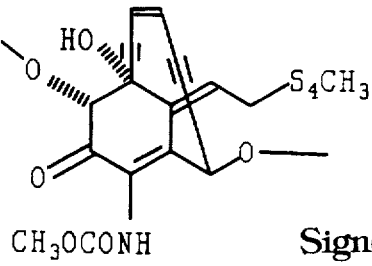

Signed and Sealed this

Twenty-second Day of June, 1993

Attest:

MICHAEL K. KIRK

Attesting Officer

Acting Commissioner of Patents and Trademarks